United States Patent
Blackadar et al.

(10) Patent No.: US 6,298,314 B1
(45) Date of Patent: Oct. 2, 2001

(54) DETECTING THE STARTING AND STOPPING OF MOVEMENT OF A PERSON ON FOOT

(75) Inventors: Thomas P. Blackadar, Natick; Paul J. Gaudet, Tewksbury; Samuel W. Joffe, Cambridge, all of MA (US)

(73) Assignee: Personal Electronic Devices, Inc., Southborough, MA (US)

( * ) Notice: Subject to any disclaimer, the term of this patent is extended or adjusted under 35 U.S.C. 154(b) by 0 days.

(21) Appl. No.: 09/364,202

(22) Filed: Jul. 30, 1999

Related U.S. Application Data

(63) Continuation-in-part of application No. 08/942,802, filed on Oct. 2, 1997, now Pat. No. 6,018,705.

(51) Int. Cl.[7] .................................................. G01C 22/00
(52) U.S. Cl. ........................ 702/178; 73/865.4; 235/105
(58) Field of Search .................... 702/178, 160; 73/865.4; 368/10; 235/105

(56) References Cited

U.S. PATENT DOCUMENTS

| | | | |
|---|---|---|---|
| 3,972,038 | 7/1976 | Fletcher et al. | 370/189 |
| 3,974,491 | 8/1976 | Sipe | 340/272 |
| 4,409,992 | 10/1983 | Sidorenko et al. | 128/782 |
| 4,499,394 | 2/1985 | Koal | 310/330 |
| 4,578,769 | 3/1986 | Frederick | 364/565 |
| 4,649,552 | 3/1987 | Yukawa | 377/24 |
| 4,651,446 | 3/1987 | Yukawa et al. | 36/132 |
| 4,745,564 | 5/1988 | Tennes et al. | 364/566 |
| 4,763,287 | 8/1988 | Gerhaeuser et al. | 364/561 |
| 4,771,394 | 9/1988 | Cavanagh | 364/561 |
| 4,774,679 | 9/1988 | Carlin | 364/550 |
| 4,814,661 | 3/1989 | Ratzlaff et al. | 310/328 |
| 4,830,021 | 5/1989 | Thornton | 128/707 |
| 4,855,942 | 8/1989 | Bianco | 364/561 |
| 4,956,628 | 9/1990 | Furlong | 340/323 |
| 4,962,469 * | 10/1990 | Ono et al. | 364/561 |
| 5,033,013 | 7/1991 | Kato et al. | 364/561 |
| 5,186,062 | 2/1993 | Roost | 73/865.4 |
| 5,269,081 | 12/1993 | Gray | 36/136 |
| 5,285,586 | 2/1994 | Goldston et al. | 36/137 |
| 5,323,650 | 6/1994 | Fullen et al. | 73/172 |
| 5,343,445 * | 8/1994 | Cherdak | 368/10 |
| 5,357,696 | 10/1994 | Gray et al. | 36/136 |
| 5,361,778 | 11/1994 | Seitz | 128/779 |
| 5,422,628 | 6/1995 | Rodgers | 340/573 |
| 5,437,289 | 8/1995 | Liverance et al. | 128/779 |
| 5,452,269 * | 9/1995 | Cherdak | 368/10 |

(List continued on next page.)

Primary Examiner—Patrick Assouad
(74) Attorney, Agent, or Firm—Wolf, Greenfield & Sacks, P.C.

(57) ABSTRACT

Various methods for monitoring movement of a person involve using a sensor to generate a signal in response to movement of a person. In one embodiment, a characteristic in the signal is identified that indicates the person is walking or running and, in response to identifying the characteristic, a timer is started. In another embodiment, after the person has begun walking or running, a characteristic in the signal is identified that indicates the person has ceased walking or running and, in response to identifying the characteristic, an action is taken. In another embodiment, a characteristic in the signal is identified that is indicative of a foot of the person being in motion and, in response to identifying the characteristic, a timer is started. In another embodiment, after a foot of the person has been in motion, a characteristic in the signal is identified that is indicative of the foot ceasing to be in motion and, in response to identifying the characteristic, an action is taken. In another embodiment, in response to identifying that the person is not walking or running, a characteristic in the signal is identified that indicates the person has begun walking or running and, in response to identifying the characteristic, an action is taken. In another embodiment, in response to identifying that a foot of the person is stationary, a characteristic in the signal is identified that indicates the foot is in motion and, in response to identifying the characteristic, an action is taken.

91 Claims, 9 Drawing Sheets

U.S. PATENT DOCUMENTS

| | | | |
|---|---|---|---|
| 5,485,402 | * | 1/1996 | Smith et al. .......................... 364/566 |
| 5,524,637 | * | 6/1996 | Erickson ............................. 128/779 |
| 5,526,290 | * | 6/1996 | Kanzaki .............................. 364/565 |
| 5,541,860 | | 7/1996 | Takei et al. .......................... 364/566 |
| 5,583,776 | | 12/1996 | Levi et al. ........................... 364/450 |
| 5,623,944 | | 4/1997 | Nashner .............................. 128/779 |
| 5,636,146 | | 6/1997 | Flentov et al. ....................... 364/569 |
| 5,720,200 | * | 2/1998 | Anderson et al. .................... 73/172 |
| 5,724,265 | | 3/1998 | Hutchings ........................... 364/565 |
| 5,897,457 | * | 4/1999 | Mackovjak ............................... 482/8 |
| 5,899,963 | * | 5/1999 | Hutchings ........................... 702/145 |
| 5,963,891 | * | 10/1999 | Walker et al. ....................... 702/150 |
| 5,976,083 | * | 11/1999 | Richardson et al. ................. 600/300 |
| 5,989,200 | * | 11/1999 | Yoshimura et al. ................. 600/587 |
| 6,018,705 | * | 1/2000 | Gaudet et al. ....................... 702/176 |
| 6,038,935 | * | 3/2000 | Fullen et al. ........................ 73/865.4 |
| 6,042,549 | * | 3/2000 | Amano et al. ....................... 600/500 |
| 6,052,654 | * | 4/2000 | Gaudet et al. ....................... 702/160 |

* cited by examiner

DETECTING THE STARTING AND STOPPING OF MOVEMENT OF A PERSON ON FOOT

This is a continuation-in-part of application Ser. No. 08/942,802, filed Oct. 2, 1997 now U.S. Pat. No. 6,018,705.

BACKGROUND OF THE INVENTION

1. Field of the Invention

The present invention relates to the monitoring of the orthopedic motion of a person and, more particularly, to the detecting of when the person starts and stops engaging in Such motion.

2. Discussion of the Related Art

One known device for monitoring the orthopedic motion of a person is a pedometer. A pedometer typically is mounted on the waist of a person and is configured to count the footsteps of the person by measuring the number of times the person's body moves up an down during footsteps taken by the person. One prior art pedometer design uses a weight mounted on a spring to count the number of times that the person's body moves up and down as the person is walking. By properly calibrating the pedometer according to a previously measured stride length of the person, the distance traveled by the person may be measured by this device.

Another prior art pedometer device uses an accelerometer to measure the number of times that a foot impacts the ground when a person is in locomotion. That is, an accelerometer is mounted on a person so as to produce a signal having pronounced downward going peaks that are indicative of moments that the person's foot impacts the ground. These devices therefore produce results similar to the prior art weight-on-a-spring pedometer devices in that they merely count the number of footsteps of a person.

Some walkers and runners find it useful to measure a time between when they begin and when they finish walking or running. Heretofore, this time measurement has been accomplished by means of a stopwatch held in the hand of a person or worn on the person's wrist. Using a stopwatch, a person can manually start a timer when he or she begins to run or walk, and can manually stop the timer when he or she stops walking or running, thereby measuring a total time that the person was in locomotion, e.g., during a particular exercise session. This manual starting and stopping of a timer can be burdensome for the person because it requires the person to physically depress a button to accomplish the same.

SUMMARY OF THE INVENTION

According to one aspect of the present invention, a method for monitoring movement of a person in locomotion on foot involves using a sensor to generate a signal in response to movement of a person. A characteristic in the signal is identified that indicates the person is walking or running. In response to identifying the characteristic, a timer is started.

According to another aspect of the invention, a system for monitoring movement of a person in locomotion on foot includes a sensor and at least one controller. The sensor generates a signal in response to movement of the person. The least one controller is configured to identify a characteristic in the signal that indicates the person is walking or running, and to, in response to identifying the characteristic, start a timer.

According to one aspect of the present invention, a method for monitoring movement of a person in locomotion on foot involves using a sensor to generate a signal in response to movement of a person. After the person has begun walking or running, a characteristic in the signal is identified that indicates the person has ceased walking or running. In response to identifying the characteristic, an action is taken.

According to another aspect of the invention, a system for monitoring movement of a person in locomotion on foot includes a sensor and at least one controller. The sensor generates a signal in response to movement of the person. The least one controller is configured to, after the person has begun walking or running, identify a characteristic in the signal that indicates the person has ceased walking or running, and to, in response to identifying the characteristic, take an action.

According to another aspect of the invention, a method for monitoring movement of a person involves using a sensor to generate a signal in response to movement of a person. A characteristic in the signal is identified that is indicative of a foot of the person being in motion. In response to identifying the characteristic, a timer is started.

According to another aspect of the invention, a system for monitoring movement of a person includes a sensor and at least one controller. The sensor generates a signal in response to movement of the person. The at least one controller is configured to identify a characteristic in the signal indicative of a foot of the person being in motion, and to, in response to identifying the characteristic, start a timer.

According to another aspect of the invention, a method for monitoring movement of a person involves using a sensor to generate a signal in response to movement of a person. After a foot of the person has been in motion, a characteristic in the signal is identified that is indicative of the foot ceasing to be in motion. In response to identifying the characteristic, an action is taken.

According to another aspect of the invention, a system for monitoring movement of a person includes a sensor and at least one controller. The sensor generates a signal in response to movement of the person. The at least one controller is configured to, after a foot of the person has been in motion, identify a characteristic in the signal indicative of the foot ceasing to be in motion, and to, in response to identifying the characteristic, take an action.

According to another aspect of the invention, a method for monitoring movement of a person in locomotion on foot involves using a sensor to generate a signal in response to movement of a person. In response to identifying that the person is not walking or running, a characteristic in the signal is identified that indicates the person has begun walking or running. In response to identifying the characteristic, an action is taken.

According to another aspect of the invention, a system for monitoring movement of a person in locomotion on foot includes a sensor and at least one controller. The sensor generates a signal in response to movement of the person. The least one controller is configured to identify that the person is not walking or running, to, in response to identifying that the person is not walking or running, identify a characteristic in the signal that indicates the person has begun walking or running, and to, in response to identifying the characteristic, take an action.

According to another aspect of the invention, a method for monitoring movement of a person involves using a sensor to generate a signal in response to movement of a person. In response to identifying that a foot of the person is stationary, a characteristic in the signal is identified that indicates the foot is in motion. In response to identifying the characteristic, an action is taken.

According to another aspect of the invention, a system for monitoring movement of a person includes a sensor and at least one controller. The sensor generates a signal in response to movement of the person. The at least one controller is configured to identify that a loot of the person is stationary, to, in response to identifying that the foot is stationary, identify a characteristic in the signal that indicates the foot is in motion, and to, in response to identifying the characteristic, take an action.

DETAILED DESCRIPTION OF THE INVENTION

In one illustrative embodiment of the invention, a sensor, e.g., a device including an accelerometer, is mounted on a person's foot so that it generates a signal when the person's foot moves. The signal from the sensor is analyzed to identify: (a) when the foot is stationary, and (b) when the foot is in motion. In one embodiment, a timer is started when it is determined that the foot is moving, and is stopped when it is determined that the foot has ceased moving. In such an embodiment, the value of the timer represents the time period of a particular athletic endeavor of the person. For example, the time period between when a person begins walking or running and when the person stops walking or running, or between when the person jumps in the air and when the person lands on the ground, can be measured.

Figure 1:
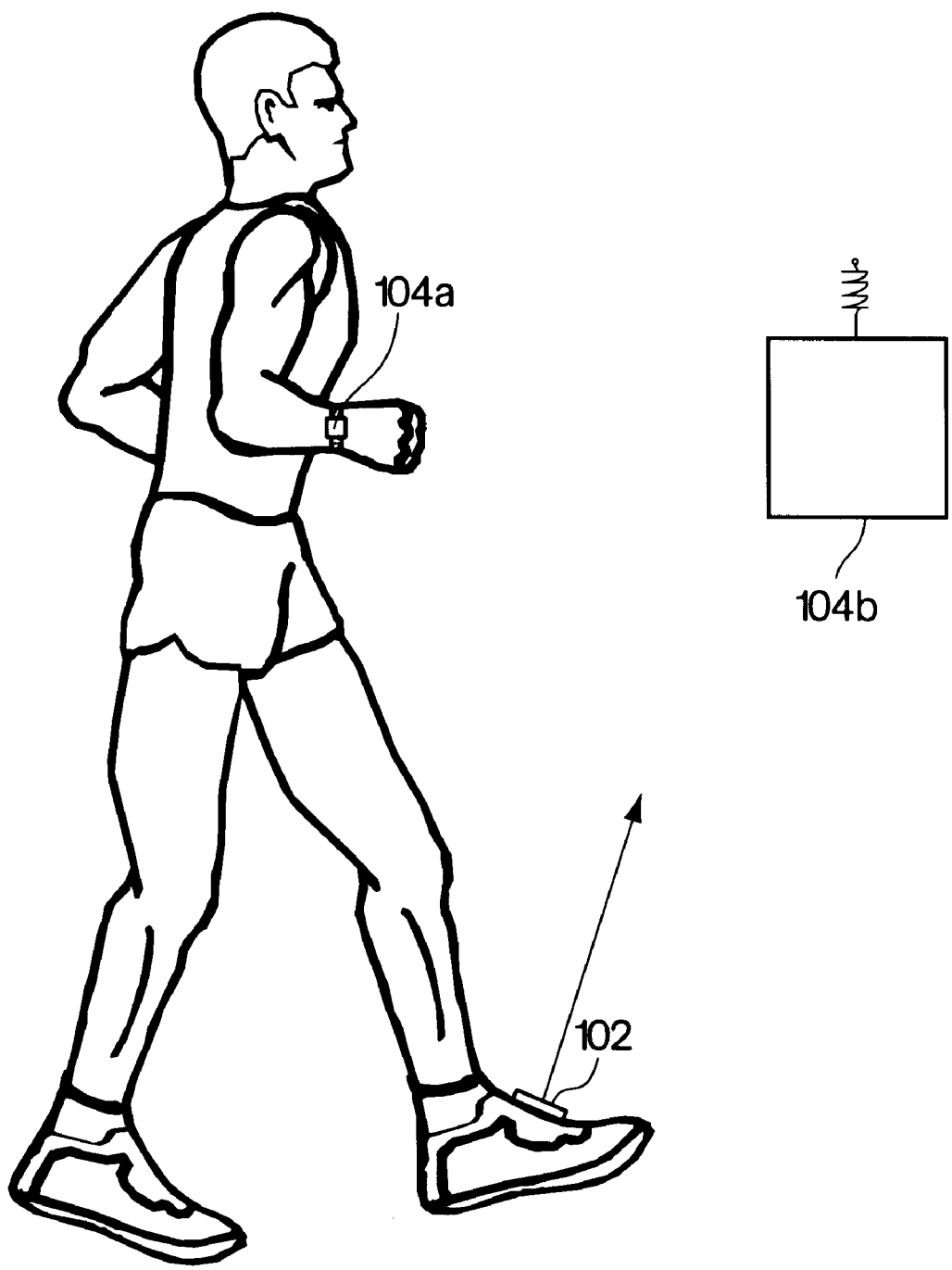
FIG. 1 is a diagram showing a motion-sensitive device mounted on a person and other network elements that may communicate with the motion-sensitive device in connection with an illustrative embodiment of the invention.

FIG. 1 illustrates how a motion-sensitive device 102 configured in accordance with an illustrative embodiment of the invention may be mounted on a person. The device 102 may sense motion in any of a number of ways, and the invention is not limited to any particular device or technique for sensing motion. In the illustrative embodiment shown, the device 102 includes an accelerometer that senses acceleration along an acceleration-sensing axis 106. In alternative embodiments, the motion-sensitive device 102 may, for example, include a pressure-sensitive resistive switch, a piezoelectric transducer, a GMR sensor, a simple contact switch, a mercury switch, or any other device capable of generating a signal in response to motion of the person.

In the example shown, the device 102 is mounted on an instep of the persons's foot such that the acceleration-sensing axis 106 is oriented normal to the instep of the foot. In this configuration, the acceleration-sensing axis 106 forms an acute angle with the surface on which the person is standing. A few examples of devices and techniques for mounting an electronic device such as the motion-sensitive device 102 to a person's shoe are described in U.S. patent application Ser. No. 09/164,654, which is hereby incorporated herein by reference. It should be appreciated, however, that the device may alternatively be mounted in other ways, anywhere else on the person, and/or at any other angle with respect to the ground, so long as it generates a signal that, for the particular application, responds appropriately to motion of the person. The device 102 may, for example, be mounted on an ankle, a wrist, the waist, or on or within a shoe worn by the person.

In addition to the motion-sensitive device 102. FIG. 1 shows network devices 104a–b that may be linked (e.g., by a radio frequency (RF) link, infrared (IR) link, hardwired connection, or the like) to the device 102 to increase or distribute the functionality of the device 102. In the FIG. 1 example, the network device 104a is mounted on a wrist of a person, and the network device 104b is positioned at a location separate from the person. An example of circuitry that may be included in each of the network devices 104a–b is described below in connection with FIG. 4. One significant function that may be performed by the network devices 104a–b is that of providing an interface between the motion-sensitive device 102 and the person using the respective network device 104. That is, the person having the motion-sensitive device 102 mounted on him/her may provide commands to the device 102 via the wrist-mounted network device 104a, rather than bending over to access the shoe-mounted device 102. Similarly, the person may receive feedback from the shoe-mounted device 102 via the wrist-mounted network device 104a, so that the person need not stop running or walking, for example, to receive such feedback. A person other than the person wearing the motion-sensitive device 102 may also, for example, provide input to or receive feedback from the motion-sensitive device 102 via the separate network device 104b.

Figure 2:
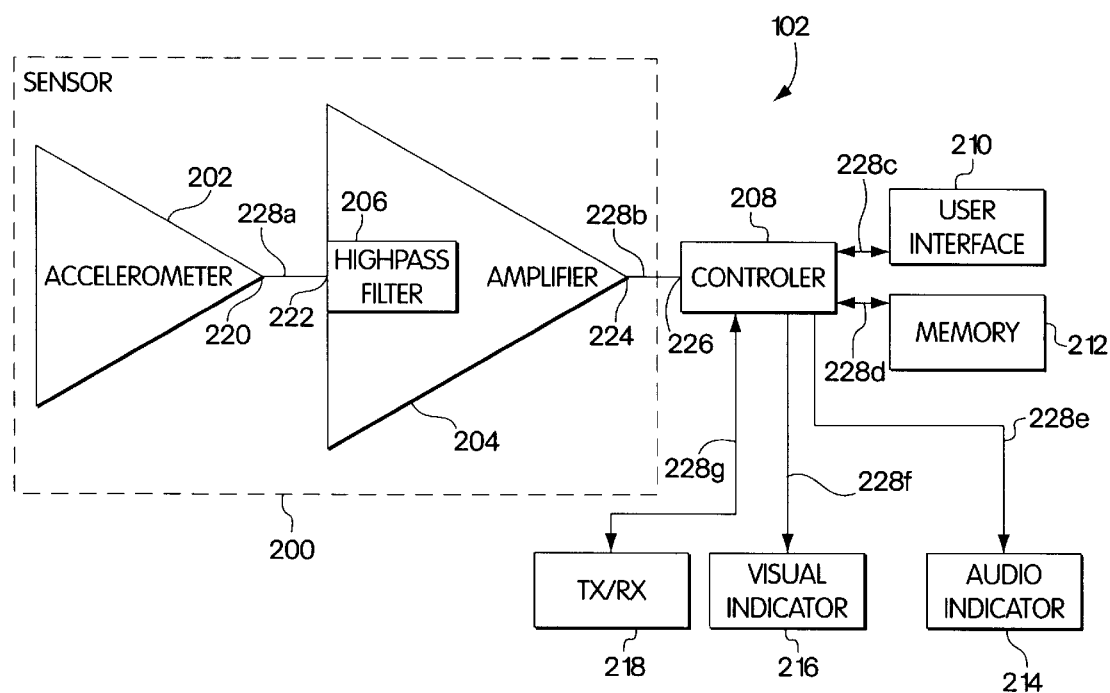
FIG. 2 is a block diagram of a motion-sensitive device that may be mounted on a person and/or used in a network such as that shown in FIG. 1 in connection with an embodiment of the invention.

FIG. 2 is a block diagram showing an illustrative embodiment of the motion-sensitive device 102 of FIG. 1. In the embodiment shown, the motion-sensitive device 102 includes a sensor 200 and a controller 208. An output 224 of the sensor 102 is coupled to an input 226 of the controller 208 to provide a signal generated by the sensor (in response to movement of the person) to the controller 208. In the embodiment shown, the sensor 200 includes an accelerometer 202 and an amplifier 204 having a high-pass filter 206 integrated therein. An output 220 of the accelerometer 202 is coupled to an input 222 of the amplifier 204 to provide the output signal of the accelerometer 202 to the input 222.

As mentioned above, an accelerometer is only one example of a number of devices that may be used to perform the motion-sensing function of the sensor 200, and the invention is not limited to the use of an accelerometer for this purpose. In embodiments that do employ accelerometers, any of numerous types of accelerometers may be used. In one embodiment, for example, the accelerometer 202 comprises part number ADXL250, manufactured by Analog Devices, Inc., of Norwood Mass. Alternatively, a simpler device capable of generating a signal in response to acceleration may be used as the accelerometer 202. For example, a simple cantilever device or weight-on-a-spring type element that generates an electric signal in response to acceleration of an object to which it is attached may alternatively be employed. In one embodiment, a piezoceramic disk of the type typically used for speaker/microphone applications is used as the accelerometer 202. In such an embodiment, the deformation of the disk in response to acceleration generates an electric signal which, after amplification and/or filtration, is sufficient to be analyzed by the controller 208 as described below. One example of such a disk is part number CD11BB, manufactured by Taiyo Yuden.

In the example embodiment of FIG. 2, the device 102 further includes a user interface 210, a memory 212, an audio indicator 214, a visual indicator 216, and a transceiver 218. The memory 212 may be used to store instructions to be executed by the controller 208. When executed by the controller 208, the stored instructions may cause the controller 208 to perform one or more routines in connection with various aspects of the invention described herein. In one embodiment, the controller 208 has virtually all circuitry, e.g., memory, timers, analog-to-digital (A/D) converters, and the like, on board, so that instructions for the controller 208 may be stored in the on-board memory. Therefore, in such an embodiment, the memory 212 is not required to store instructions for the controller 208, but may be still be used, if desired, to perform functions such as permanently storing data produced controller 208.

The user interface 210 may be activated manually by means of buttons, switches or other physically actuated devices, or may be voice activated using a commercially available voice activation device. As discussed in more detail below, the user interface 210 may be used, for example: (1) to adjust any of several parameters used in a software routine performed in connection with the invention, (2) to select any of several possible outputs for the user, e.g., outputs to be displayed on the visual indicator 216, or audio signals to be provided via audio indicator 214, and/or (3) to initiate software routines performed in connection with the invention.

As discussed in more detail below, the transceiver 218 may, for example, be an RF transceiver used to communicate, e.g., using a network protocol, with corresponding transceivers included in the devices 104a–b. In this regard, it should be appreciated that any of the communication links 228a–g between the components of the device 102 may also be implemented using RF, IR or any other wireless communication medium, and need not be implemented using hardwired connections.

Figure 3:
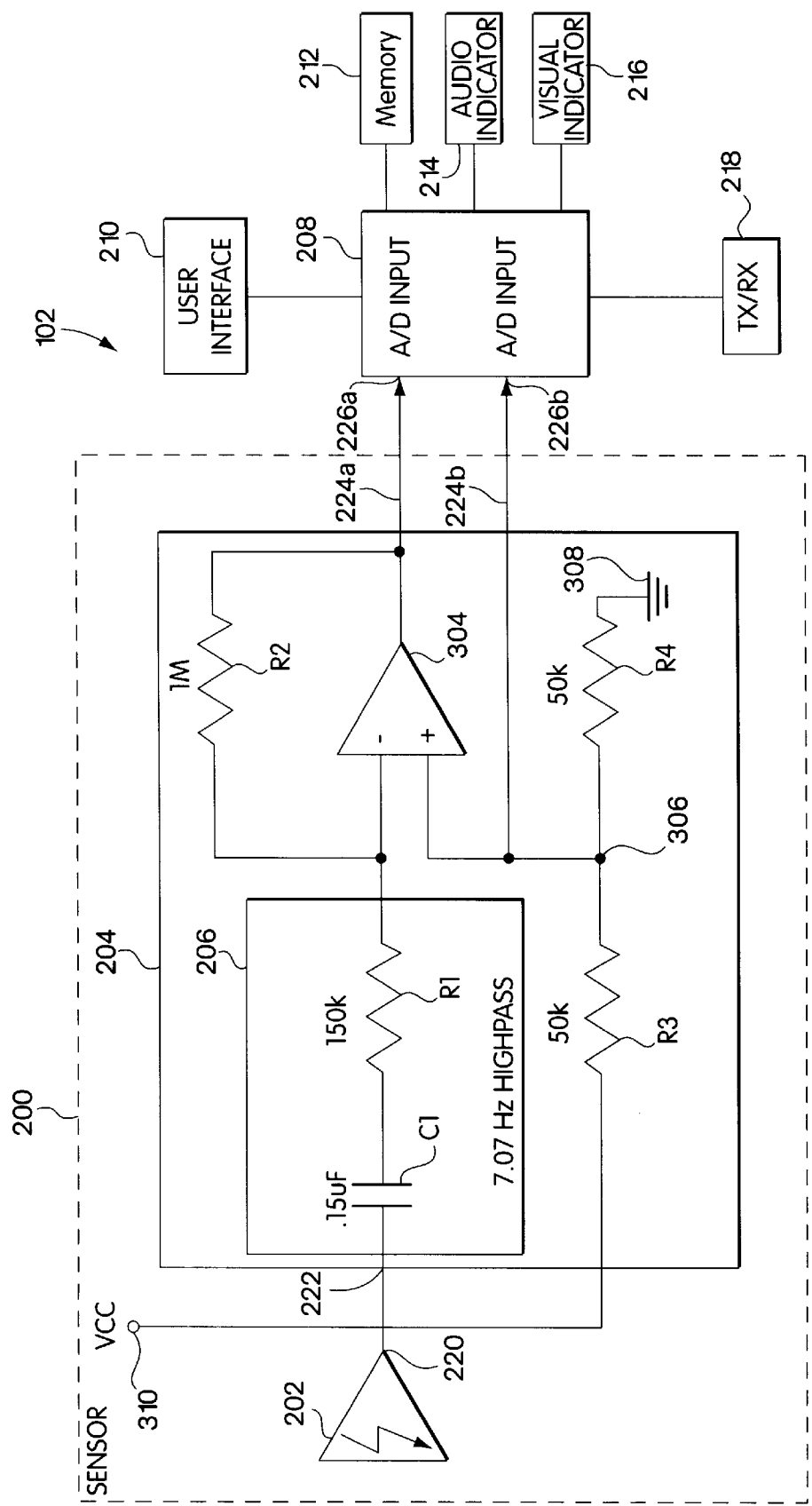
FIG. 3 is a schematic diagram of circuitry that may be included in several of the blocks of FIG. 1 in connection with an embodiment of the invention.

FIG. 3 shows the motion-sensitive device 102 of FIG. 2 in more detail. As shown, the output 220 of the accelerometer 202 is provided to an input capacitor C1 included in the amplifier 204. The amplifier 204, in the embodiment shown, further includes an operational amplifier 304 and resistors R1–R4. The operational amplifier 304 may comprise, for example, part number MAX418 produced by MAXIM, Inc. As shown in FIG. 3, the resistor R1 is connected between the input capacitor C1 and the inverting input of the operational amplifier 304, and the resistor R2 is connected in feedback between the inverting input terminal and the output 224a of the operational amplifier 304. Thus, the combination of the input capacitor C1 and resistor R1 forms a high-pass filter, and the position of resistors R1 and R2 place the amplifier circuit in an inverting configuration with a gain-factor dependent on the relative values of resistors R1 and R2. In the embodiment shown, resistor R2 has a value of one mega-ohm and resistor R2 has a value of "150" kili-ohms, so that the gain factor of the amplifier is approximately "−6.6". In addition, in the embodiment shown, the capacitor C1 has a value of "0.15" microfarads, so that the high-pass filter 206 of the amplifier 204 cuts off input signal frequencies that are less than approximately "7.07" hertz.

The resistor R3 is connected between a VCC supply node 310 and a non-inverting input 306 of the operational amplifier 304, and the resistor R4 is connected between the non-inverting input 306 and a ground node 308. The VCC supply node 310 is maintained at approximately five volts (e.g., regulated from a six-volt battery) in relation to the ground node 308, and the resistors R3 and R4 are of equal values (e.g., fifty kili-ohms each) so that the voltage at the non-inverting input node 306 is maintained approximately midway between the voltage at the VCC supply node 310 and the ground node 308 (i.e., approximately "2.5" volts).

A first output 224a of the amplifier 204 is connected to a first A/D input 226a of the controller 208, and a second output 224b of the amplifier 204 is connected to a second A/D input 226b of controller 208. In one embodiment, the controller 208 may comprise part number PIC:16C73, manufactured by Microchip, Inc. This micro-controller includes onboard memory, A/D converters, and timers. The A/D input 226b of the controller 208 serves as a zero-reference that is maintained at approximately "2.5" volts (as described above), and the input 226a of the controller 208 serves as a variable input that can fluctuate between zero and five volts. The controller 208 may sample the voltages at the inputs 226a–b at a rate of approximately five-hundred samples-per-second, may convert these samples into 8-bit unsigned digital values, and may calculate the difference between the voltages at the two inputs 226a–b, which difference is used during operation of a software routine described below in connection with FIG. 9.

In embodiments wherein the voltage at each of the inputs 226a–b (FIG. 3) of the controller 208 is converted to an 8-bit digital value, the amplitude of the voltage at each input will be represented as one of "256" discrete levels. Also, because resistors R3 and R4 create a voltage at node 306 that is approximately half-way between the high-supply voltage of five volts and the ground, i.e., at approximately "2.5" volts, the zero reference at the input 226b will remain near the midpoint of the "256" levels, i.e., at approximately level "128."

Figure 4:
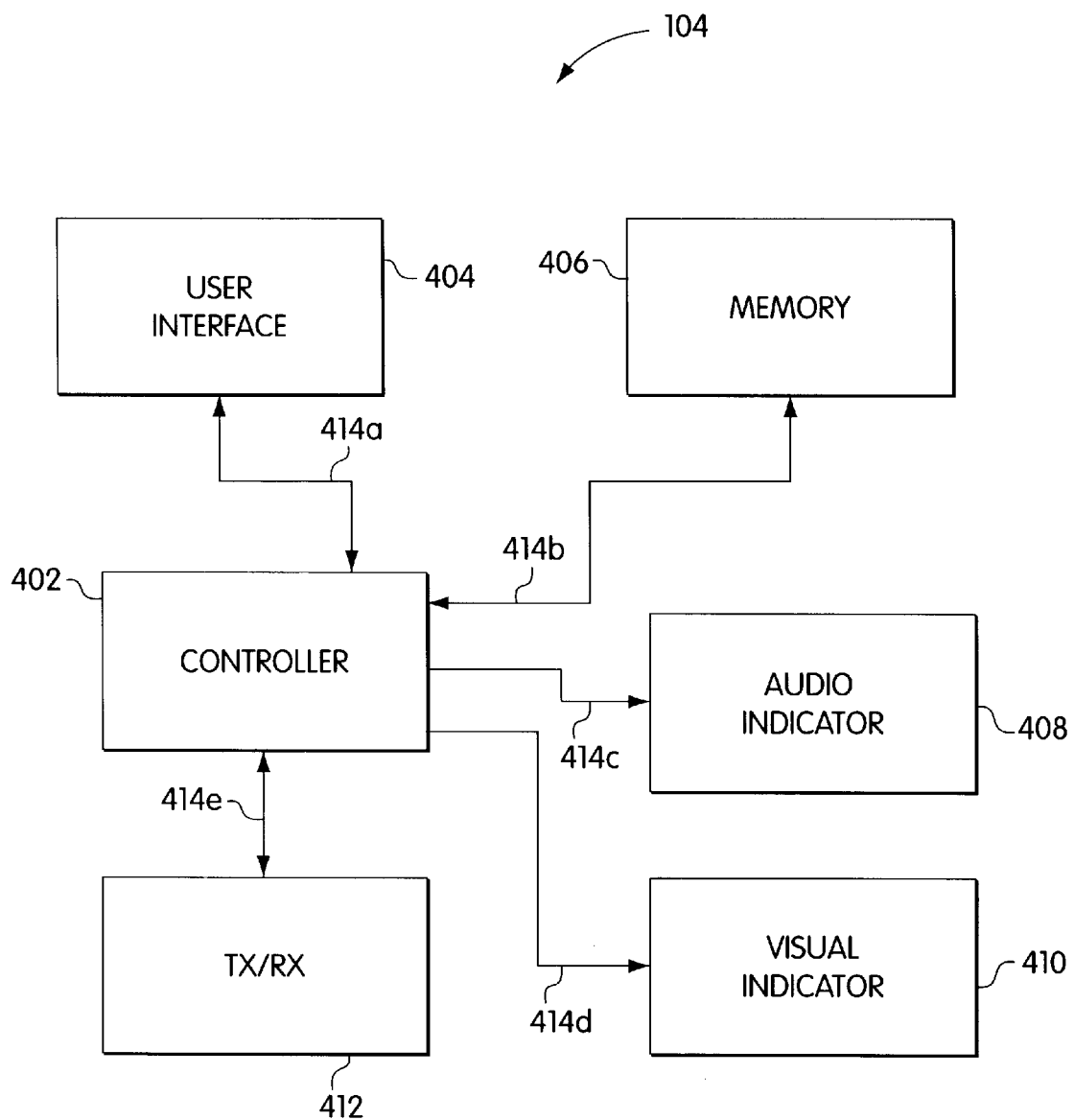
FIG. 4 is a block diagram of one of the network devices of FIG. 1 that may communicate with the motion-sensitive device in connection with an embodiment of the invention.

FIG. 4 shows a block diagram of an illustrative embodiment of one of the networked devices 104a–b of FIG. 1. As shown each network device 104 may include a controller 402, a user interface 404, a memory 406, an audio indicator 408, a visual indicator 410, and a transceiver 412. Each of these devices may operate similarly to the corresponding devices shown in FIGS. 2–3. The controller 402 may, for example, execute instructions stored in the memory 406 to perform various routines, or may execute instruction stored in an on-board memory. In the example shown, the network device 104 can use the transceiver 412 to communicate, e.g., using a network protocol, with the motion-sensitive device 102 and/or the other network device 104. As mentioned above, this communication can be useful in that it can permit a user to interface with, e.g., provide commands to, the motion-sensitive device 102 via the user interface 404 and/or to receive feedback from the device 102 via the audio and visual indicators 408 and 410. As with the motion-sensitive device 102, any of the communication links 414a–c between the components of a network device 104 may also be implemented using RF, IR, or any other wireless communication medium, and need not be implemented using hardwired connections.

Figure 5A:
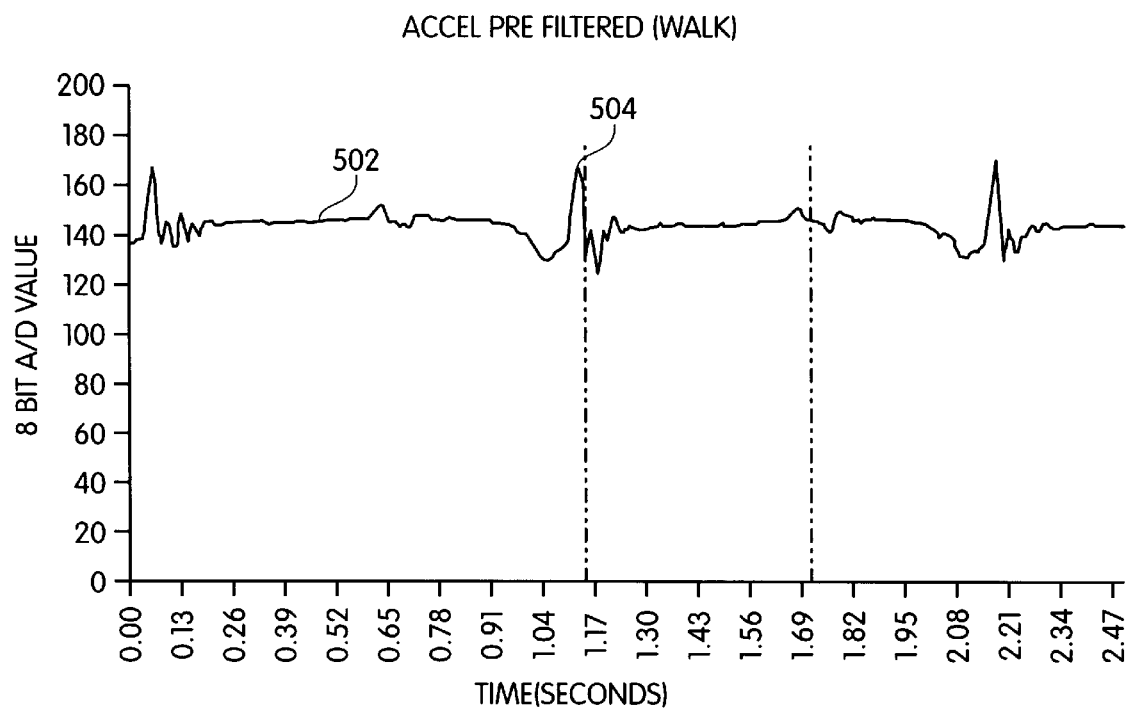
FIG. 5 is a pair of graphs showing signals at two nodes of the circuit shown in FIG. 3 during a time period when a person is walking.
Figure 5B:
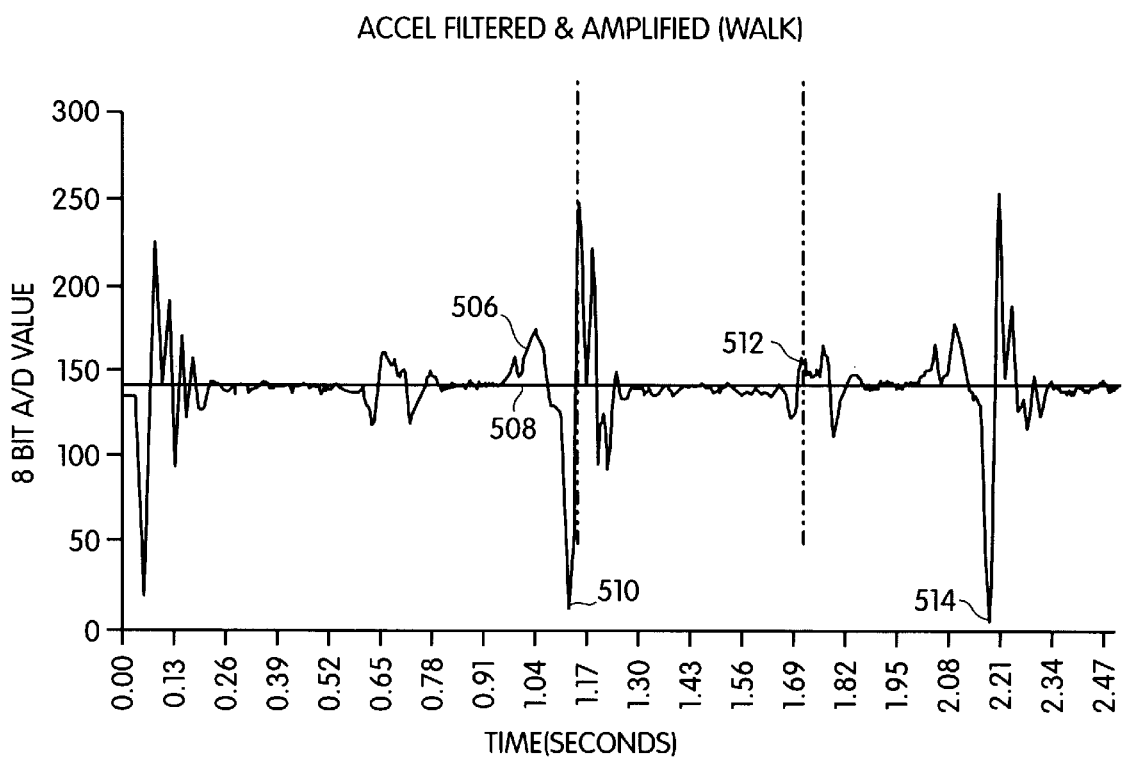

FIG. 5 shows curves representing the 8-bit unsigned digital values of the voltages at the nodes 220 and 224a of the circuit shown in FIG. 3 during a period when a person is walking. That is, the curve 502 in FIG. 5 represents (digitally) the voltage at the output 220 of accelerometer 202 before it is filtered and amplified, and the curves 506 and 508, respectively, represent (digitally) the voltages at the inputs 226a and 226b of the controller 208 during the period when the person is walking. While each of the curves 506, 508 and 502 shares a common time axis, the voltage-magnitude axis of the curves 506 and 508 is distinct from the voltage-magnitude axis of the curve 502. Therefore, the placement of the curve 502 above the curves 506 and 508 is not intended to signify that the curve 502 attains a higher amplitude than do the curves 506 and 508.

As shown in FIG. 5, because the amplifier 204 is configured to have a negative gain-factor, a high peak 504 of the curve 502 corresponds with a low peak 510 of the curve 506. A high peak 512 of the curve 506, however, does not appear to correspond to a low peak of the curve 502. That is, the high peak 512 is readily ascertainable only after the output of accelerometer 202 has been high-pass filtered and amplified by the amplifier 204. The high peak 512 in the curve 506 indicates a moment that a foot of the person has left the surface when the person is in locomotion. Similarly, the low peak 510 in the curve 506 indicates a moment that a foot of the person has impacted with the surface when the person is in locomotion.

Figure 6A:
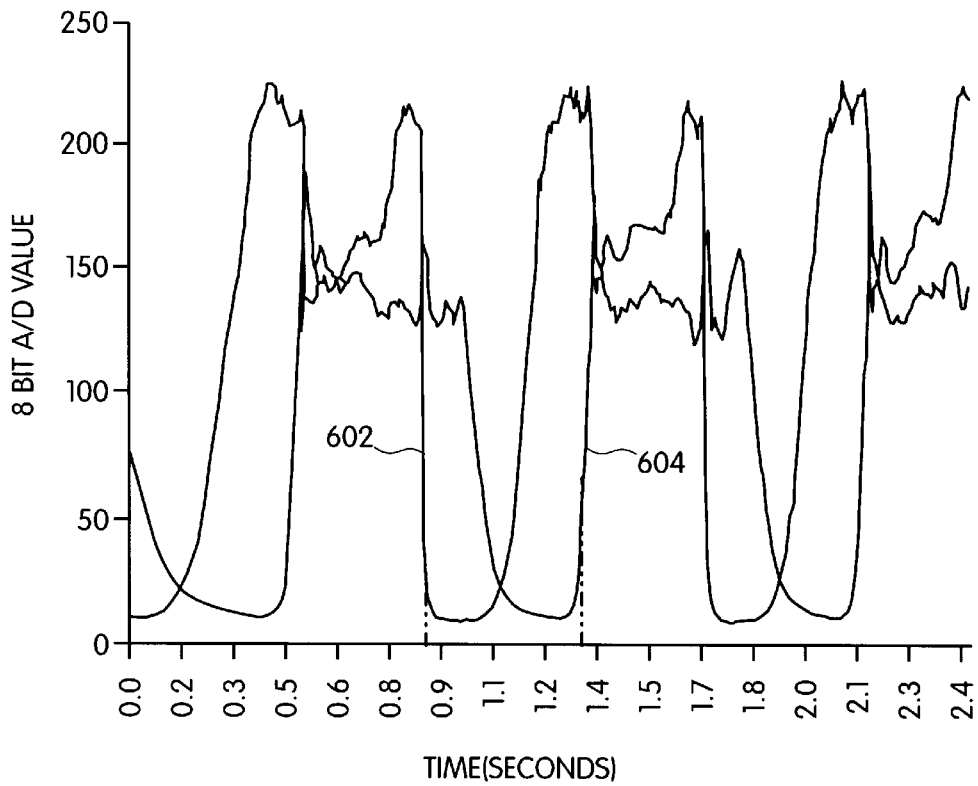
FIG. 6 is a pair of graphs that compare the amplified/filtered output of the accelerometer of FIG. 3 with signals generated using resistive sensors located in the heel and toe portions of a person's shoe during a time period when the person is walking.
Figure 6B:
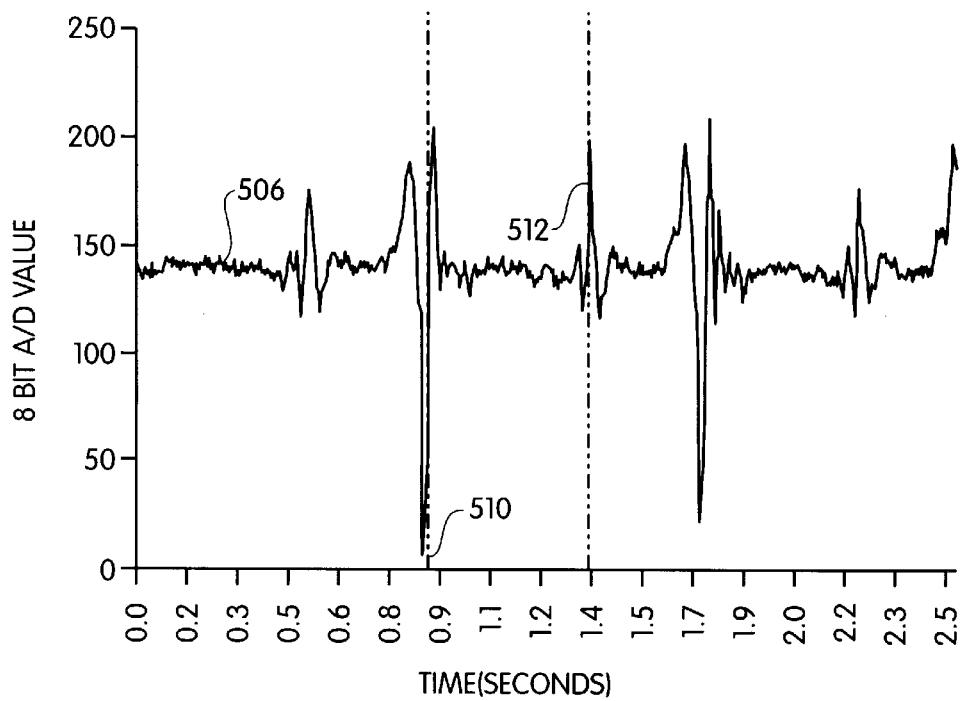

FIG. 6 shows the correspondence, when a person is walking, between (1) two curves 602 and 604 representing signals produced by resistive sensors mounted in the heel and toe portions, respectively, of a shoe, and (2) a curve 506 representing a signal produced at the output of the sensor 200 of FIG. 3. That is, the curve 602 represents the output of a resistive sensor mounted in the heel portion of a shoe, the curve 604 represents the output of a resistive sensor mounted in the toe portion of the shoe, and the curve 506 represents the voltage between the outputs 224a–b of the sensor 200. All of these measurements were taken while a person was walking. While each of the curves 602, 604 and 506 shares a common time axis, the voltage-magnitude axis of the curves 602 and 604 is distinct from the voltage-magnitude axis of the curve 506. Therefore, the placement of the curves 602 and 604 above the curve 506 is not intended to signify that the curves 602 and 604 attain higher amplitudes than does the curve 506.

As shown by the dashed lines in FIG. 6, the high-to-low transition of the curve 602 (which indicates that the shoe of the person has impacted with the ground) corresponds with the low peak 510 of the curve 506, and the low-to-high transition of the curve 604 (which indicates that the shoe of the person has left the ground) corresponds with the high peak 512 of the curve 506.

Figure 7A:
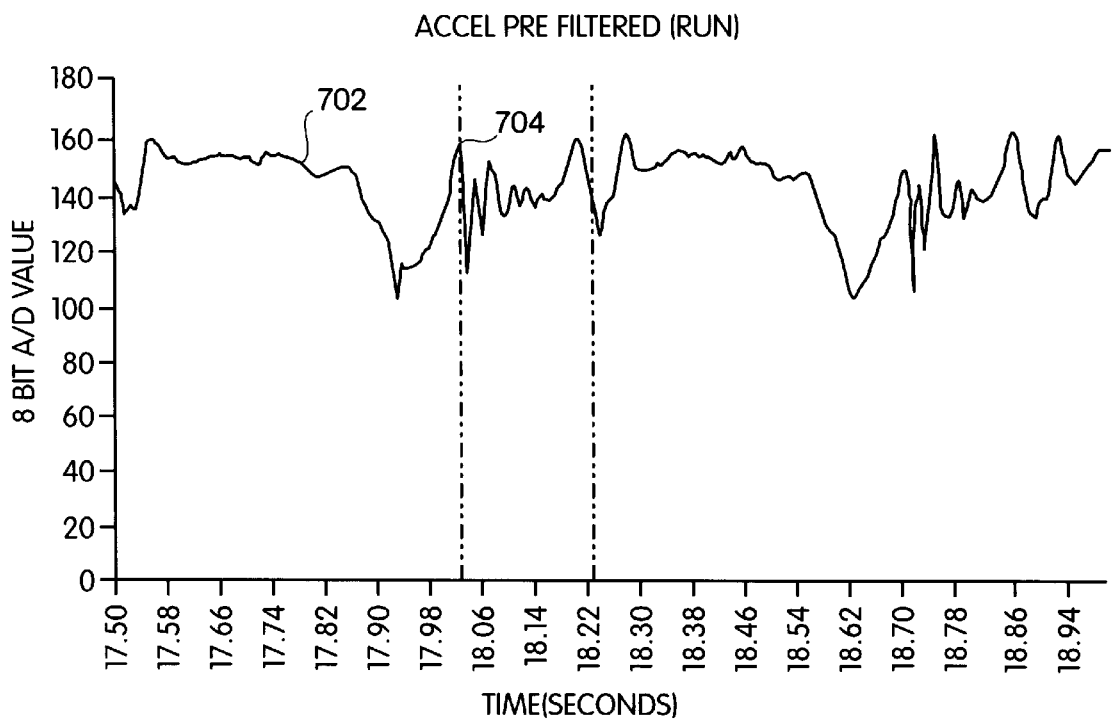
FIG. 7 is a pair of graphs showing signals at two nodes of the circuit shown in FIG. 3 during a time period when a person is running.
Figure 7B:
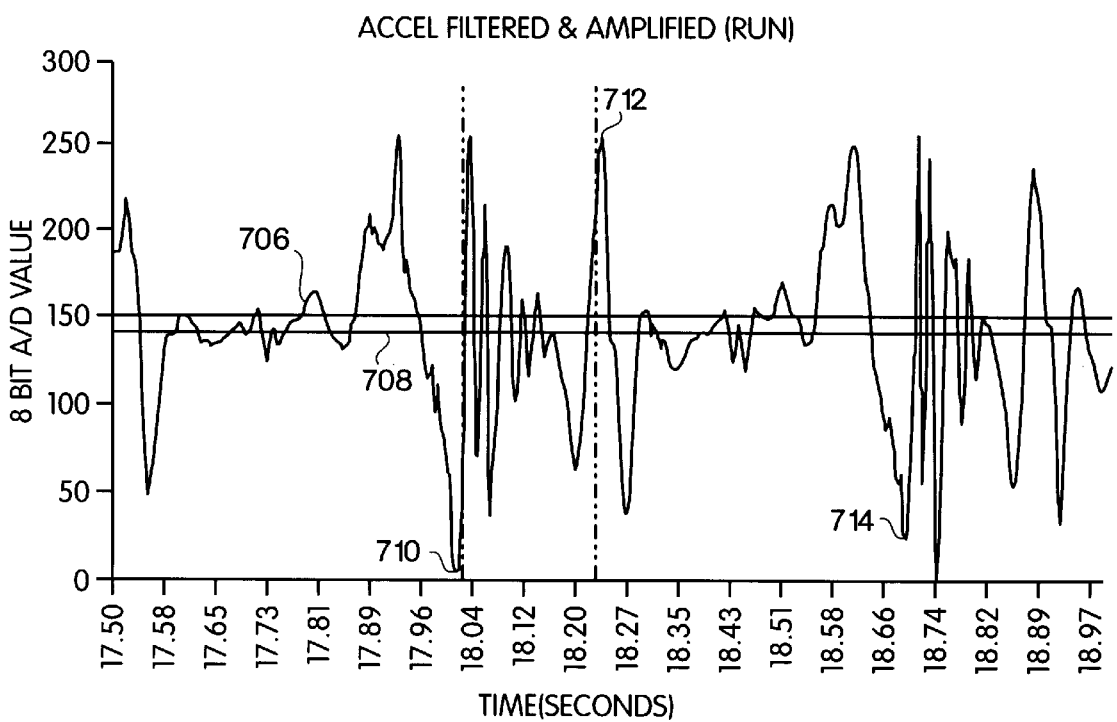

FIG. 7 shows curves representing the 8-bit unsigned digital values of the voltages at nodes 220 and 224a of the circuit shown in FIG. 3 during a period when a person is running. That is, the curve 702 in FIG. 7 represents the voltage at output 220 of the accelerometer 202 before it is filtered and amplified, and the curves 706 and 708, respectively, represent the voltages at the inputs 226a–b of the controller 208 during the period when the person is running. While each of the curves 706, 708, and 702 shares a common time axis, the voltage-magnitude axis of the curves 706 and 708 is distinct from the voltage-magnitude axis of the curve 702. Therefore, the placement of the curve 702 above the curves 706 and 708 is not intended to signify that the curve 702 attains a higher amplitude than do the curves 706 and 708.

As shown in FIG. 7, because the amplifier 204 is configured to have a negative gain-factor, a high peak 704 of the curve 702 corresponds with a low peak 710 of the curve 706. A high peak 712 of the curve 706, however, does not appear to correspond to a low peak of the curve 702. That is, the high peak 712 is readily ascertainable only after the output of the accelerometer 202 has been high-pass filtered and amplified by the amplifier 204. The high peak 712 in the curve 706 indicates a moment that a foot of the person has left the ground when the person is running. Similarly, the low peak 710 in the curve 706 indicates a moment that the foot of the person has impacted with the ground when the person is running.

Figure 8A:
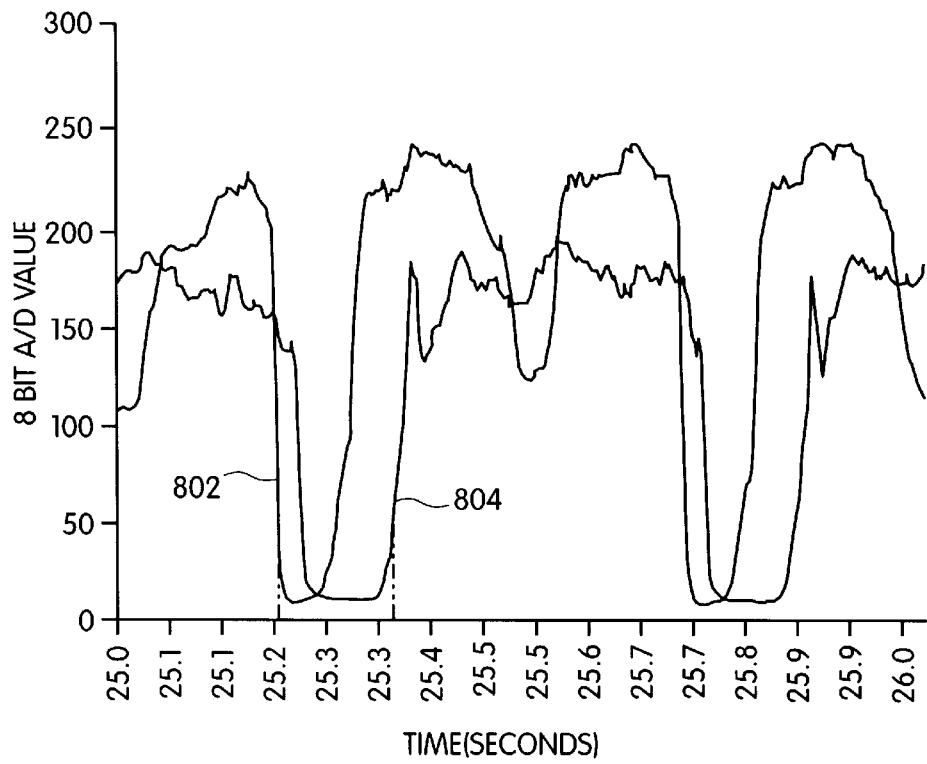
FIG. 8 is a pair of graphs that compare the amplified/filtered output of the accelerometer of FIG. 3 with signals generated using resistive sensors located in the heel and toe portions of a person's shoe during a time period when the person is running.
Figure 8B:
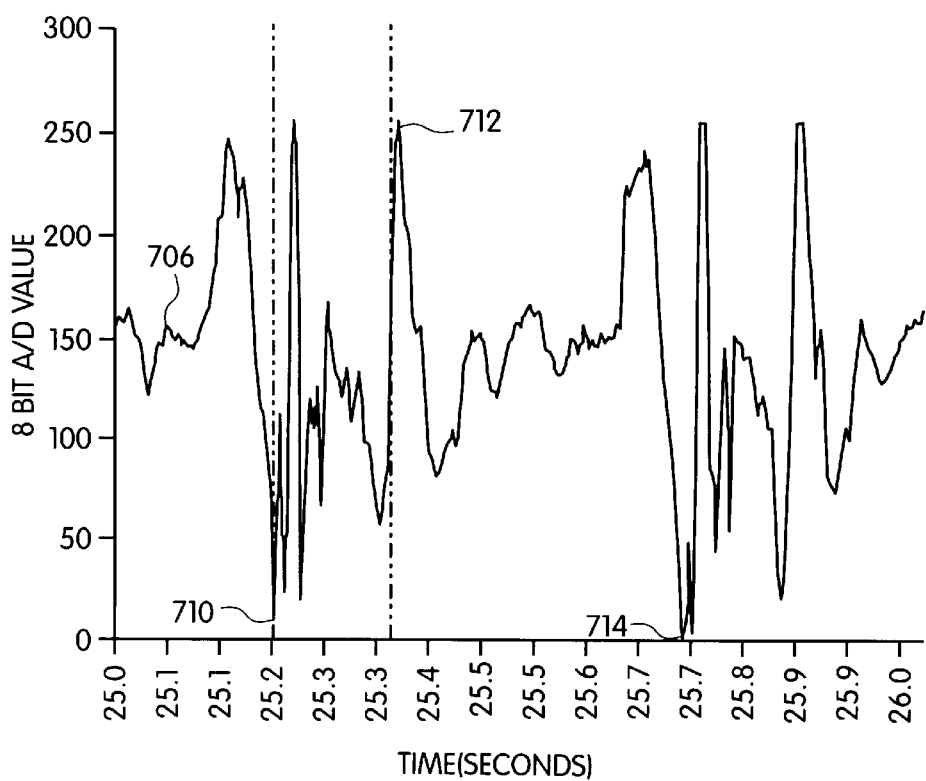

FIG. 8 shows the correspondence, when a person is running, between (1) two curves 802 and 804 represent signals produced by resistive sensors mounted in the heel and toe portions, respectively, of a shoe, and (2) the amplified and filtered output of the output of the sensor 200 of FIG. 3. That is, the curve 802 represents the output of a resistive sensor mounted in the heel portion of a shoe, the curve 804 represents the output of a resistive sensor mounted in the toe portion of the shoe, and the curve 706 represents the voltage between the outputs 224a–b of the sensor 200. All of these measurements were taken while a person was running. While each of the curves 802, 804 and 706 shares a common time axis, the voltage-magnitude axis of the curves 802 and 804 is distinct from the voltage-magnitude axis of the curve 706. Therefore, the placement of the curves 802 and 804 above the curve 706 is not intended to signify that the curves 802 and 804 attain higher amplitudes than does the curve 706.

As shown by the dashed lines in FIG. 8, the high-to-low transition of the curve 802 (which indicates that the shoe of the person has impacted with the ground) corresponds with the low peak 710 of the curve 706, and the low-to-high transition of the curve 804 (which indicates that the shoe of the person has left the ground) corresponds with the high peak 712 of the curve 706.

The output signal the sensor 200 (FIGS. 2–3) may be analyzed by the controller 208 using any of a number of software routines. Examples of routines that may be used to analyze the signal to monitor the signal to determine the speed/pace of a person, and to determine the distance traveled by the person, while walking or running, are disclosed in co-pending U.S. application Ser. No. 08/942, 802, filed Oct. 2, 1997, now U.S. Pat. No. 6,018,705, which is hereby incorporated herein by reference.

The routines performed by the controller 208 may be written in any software language and preferredly are stored in the on-board memory (not shown) of the controller 208. It should be appreciated that the functionality of such software routines may be distributed among various controllers in a network, e.g., the network of FIG. 1, and need not all be executed using the controller 208. For example, some of the functionality of the routines performed may be executed using the controller 402 (FIG. 4) of one (or both) of the devices 104a–b, in addition to the controller 208 of the device 102 (FIGS. 2–3).

Figure 9:
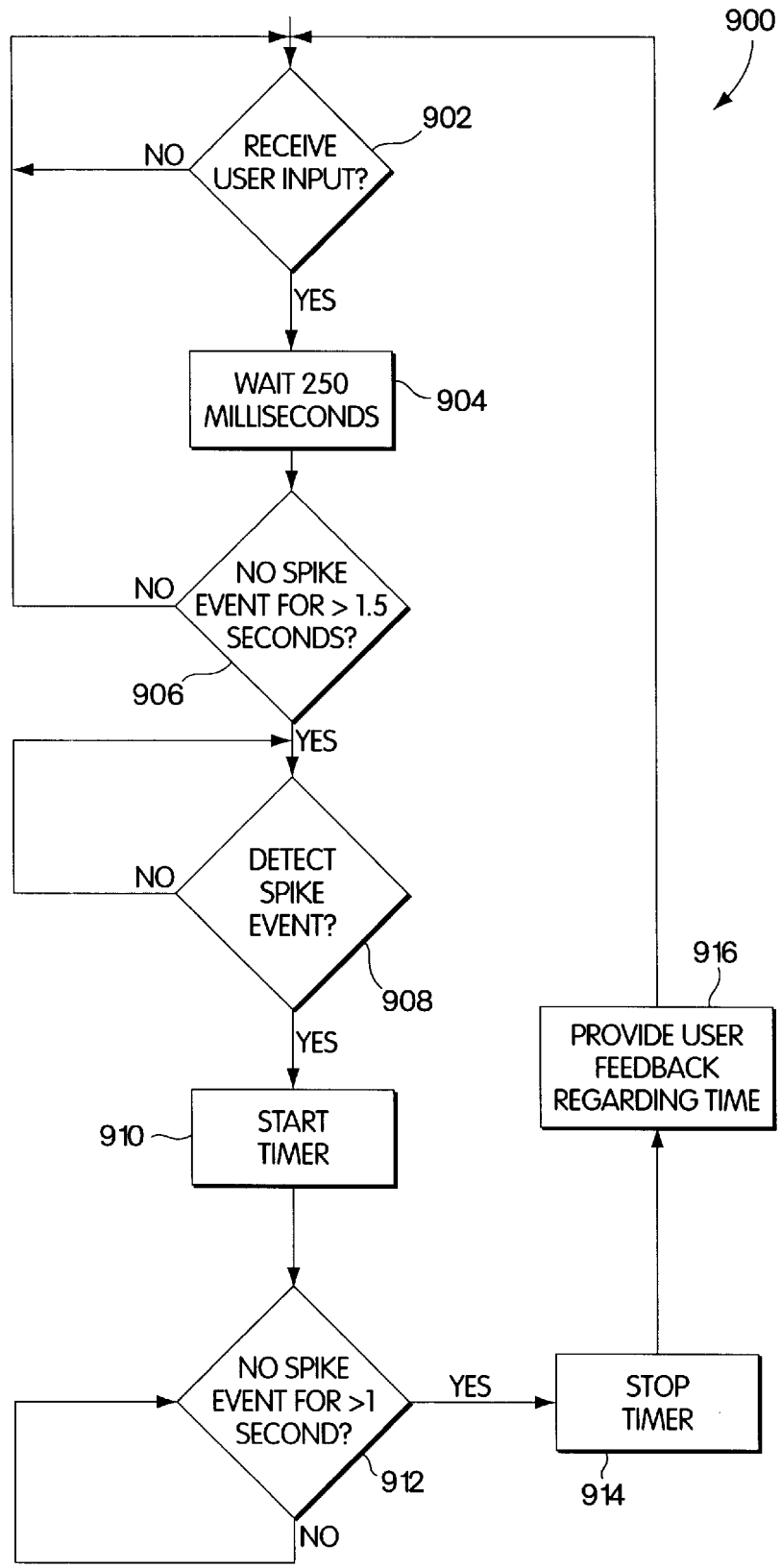
FIG. 9 is a flow diagram of a method that may be performed in connection with an illustrative embodiment of the invention.

Referring now to FIG. 9, a flow chart of a routine 900 that may be performed by the controller 208 and/or other controllers in a network is shown. Alternatively, of course, the routine 900 can be implemented using dedicated hardware, or any combination of hardware and software capable of achieving a similar result. With regard to the illustrative routine 900 of FIG. 9, it should be appreciated that the precise order of the method steps is not critical, and that the invention is not limited to embodiments that perform method steps precisely in the order shown. Additionally, it should be appreciated that the method steps shown in FIG. 9 represent only one of numerous possible routines that can achieve the desired result, and the invention is not limited to the particular routine shown. Further, it should be understood that some embodiments of the invention can perform fewer than all of the functions performed by the method steps illustrated in FIG. 9, and the invention is not limited to embodiments that employ all of the functions performed by the illustrated routine.

As shown in FIG. 9, the routine 900 may begin at a step 902, wherein it is determined whether a user has provided a particular input. This input may, for example, be provided by the user interface 210 of the motion-sensitive device 102 or by the user interface 412 of one of the network devices 104a–b. The person may, for example, depress a certain button to provide the particular input the step 902 is waiting to detect. In one embodiment, the person depresses the button when he or she wishes to begin an event such as running, walking, jumping, etc.

When it is determined (at the step 902) that the appropriate user input has been received, the routine 900 may proceed to the step 904, wherein the routine 900 may wait a predetermined amount of time (e.g., "250" milliseconds) before proceeding to the step 906. This waiting period may, for example, give the person an opportunity to become settled (i.e., to stop moving) after depressing a button or otherwise providing the user input that satisfied the step 902.

After the waiting period of the step 904, the routine may proceed to the step 906, wherein the voltage between the inputs 226a–b of the controller 208 (i.e., a signal generated by the sensor 200) may be analyzed and it may be determined whether a characteristic in the signal indicates that the person has not yet begun the event. In one embodiment, this characteristic in the signal is the absence of a positive voltage spike in the signal that exceeds a particular threshold (a "positive spike event") for a predetermined period of time. In such an embodiment, the voltage between the inputs 226a–b of the controller 208 may be analyzed to identify positive spikes that exceed a level that would occur when the foot of the person on which the device 102 is mounted were subjected to an acceleration force greater than one gravitational unit (G) in an upward direction. In an embodiment wherein the device 106 is mounted on a person's foot as shown in FIG. 1, this level may, for example, correspond to ten levels (of the "256" possible voltage levels) higher than the zero reference level at the input 226b. Positive spike events may, for example, correspond to the positive peaks 512 and 712 in the signals of FIGS. 5 and 7, respectively. If no positive spike events are identified for the predetermined period of time (e.g., "1.5" seconds), it is determined that the person has not yet begun the event. If the event to be engaged in is walking or running, for example, the lack of a positive spike event indicates that the person's foot has not yet left the ground to begin walking or running, i.e., the person's foot has remained stationary for the measured period of time. If the event to be engaged in is jumping, the lack of a positive spike event indicates that the person's foot has not yet left the ground during a jump by the person. In one embodiment, during this "1.5" second period of time, an audio, visual, or other indication is given to the person indicating that the person should not yet begin the event. For example, the device 102 may simply remain silent or illuminate no lights until the "1.5" second period has elapsed, and then may output an audio signal or illuminate a light (e.g., a green light) informing the person he or she can begin the event when ready. Alternatively, different sounds may be emitted or different lights may be illuminated (e.g., red and green lights) during the "1.5" second waiting period and when the person is given the indication to begin the event when ready.

It should be appreciated that characteristics in the signal other than the absence of a positive spike event may also indicate that the person has not yet begun walking or running and/or that the person's foot has remained stationary. For example, the signal can be monitored for the absence of a negative spike event (which, when the motion-sensitive device 102 is mounted on the person's foot as shown in FIG. 1, is indicative of the person's foot impacting with the ground) as such an indication. Negative spike events may, for example, correspond to the negative peaks 510, 514, 710, and 714 in the signals of FIGS. 5 and 7. In one embodiment, a negative spike event occurs when the voltage at the input 226a of the controller 208 is more than fifty levels (of the 256 possible digital levels) below the voltage at the zero-reference input 226b. Alternatively, the signal can be examined for the absence of both positive and negative spike events.

In the embodiment shown, when a spike event (or other characteristic in the signal from the sensor 200 indicative of the person's foot moving and/or the person beginning to walk or run) occurs within "1.5" seconds of the routine 900 reaching the step 906, the routine 900 proceeds back to the step 902. If no spike event (or other relevant characteristic in the signal) is detected for a period of "1.5" seconds, then the routine 900 may proceed to step 908, wherein the signal from the sensor is again analyzed to identify a spike event or other characteristic in the signal indicative of the person's foot moving and/or the person beginning to walk or run. Examples of characteristics indicative of the person's foot moving and/or the person walking or running are discussed above in connection with the step 906, wherein the absence of one or more of such characteristics was monitored.

At the step 908, in the embodiment shown, the routine 900 continues looking for a spike event or other relevant characteristic in the signal until it identifies such a characteristic. It may be desirable to incorporate a timeout period into the step 908, after which the step 908 returns to the step 902 if it does not identify a relevant characteristic in the signal within a particular period of time (e.g., five seconds). When a spike event or other relevant characteristic in the signal is detected in the step 908, the routine 900 may proceed to a step 910, wherein a timer is started. The timer which is started may, for example, be one of the onboard timers of the controller 208 (FIGS. 2–3) or the controller 402 (FIG. 4). In one embodiment wherein the sensor is mounted on the person's foot as shown in FIG. 1, the only characteristic looked for in the signal is the positive spike event discussed above. Therefore, in such an embodiment, the timer is started (step 910) only after a determination has been made (in step 908) that the person's foot has left the ground (e.g., by identifying one of the positive peaks 512 and 712 in the signals of FIGS. 5 and 7). Be detecting a positive spike event as the characteristic that starts the timer, the timer may be started when the person's foot first leaves the ground to begin walking or running, or when the person's foot leaves the ground during a jumping event. It should be appreciated that the starting of a timer is only one example of an action that can be taken in response to the spike event or other relevant characteristic in the sensor signal being identified in the step 908, and that the invention is not limited to the starting of a timer in such a situation. For example, a particular software routine may be initiated in lieu of or in addition to starting a timer, or any other action may be taken.

After the timer is started or other appropriate action is taken in the step 910, the routine 900 may proceed to a step 912, wherein the signal is again analyzed to identify one or more characteristics in the signal that indicate the person has completed the event. The identified characteristic(s) may be any of a number of characteristics of the signal, and the invention is not limited to the identification of any particular type of characteristic. The characteristic may, for example, identify that the person's foot has ceased moving and/or that the person has ceased walking or running. In one embodiment, this characteristic is the absence of a spike event (e.g., a positive spike event) that exceeds a particular threshold for a given period of time. For example, when the motion-sensitive device 102 is mounted on the foot of a person as shown in FIG. 1, the step 912 can monitor the signal for positive spike events (e.g., the positive peaks 512 and 712 in the signals of FIGS. 5 and 7). If no positive spike events are detected for a time period greater than one second, for example, it can be determined that the characteristic of the signal is present. As discussed above in connection with step 906, other characteristics in the signal can alternatively or additionally be analyzed to determine that the person's foot is not moving and/or that the person is no longer in no longer walking or running. For example, the absence of negative spike events (e.g., the negative peaks 510, 514, 710, and 714 in the signals of FIGS. 5 and 7) for a period of time (e.g., one second) may indicate that this situation has occurred.

If the event being performed is a jumping event, the signal may be monitored for a characteristic indicative of the person completing the jump. For example, the signal may be monitored for a negative spike event (as discussed above) which would reflect a moment that the person's foot first came into contact with the ground when the person completed the jump. Therefore, although not shown in FIG. 9, the timer started in the step 910 may be stopped in response to detecting a negative spike event, rather than detecting the absence of spike events as is done in the step 912. In this manner, the timer may reflect the amount of time the person was in the air during the jump.

As shown in FIG. 9, if (at the step 912) a spike event or other relevant characteristic in the signal from the sensor 200 occurs within one second of the last spike event or other relevant characteristic in the signal, the routine 900 may continue analyzing the signal to identify the absence of such characteristics for more than one second. If (at the step 912) no spike event or other relevant characteristic occurs for more than one second, the routine 900 may proceed to the step 914, wherein a timer is stopped or another appropriate action is taken. The timer stopped at the step 914 may, for example, be the same timer that was started at the step 910. In such a situation, the time that elapsed between when the timer started (step 910) and when the timer stopped (step 914) corresponds to an amount of time that the person was engaged in the event being monitored, e.g., walking, running, jumping etc. In one embodiment, one second is subtracted from the total elapsed time to account for the maximum time that the routine 900 may have waited at the step 912 after the person stopped walking or running and/or the person's foot stopped moving.

The timer stopped at the step 914 may also be different than the timer started at the step 910, or may have been started manually or automatically other than in connection with the method step 910. For example, a person may have manually started the timer previously (e.g., by depressing a user input button of the user interface 210 (FIG. 2) or the user interface 404 (FIG. 4)) at a time when the person was already walking or running. As discussed above in connection with the step 910, it should be appreciated that one or more actions in addition to or in lieu of starting a timer may be performed in response to the criteria of the step 912 being satisfied, and the invention is not limited to the starting of a timer as the action that is taken. As mentioned above, one example of an alternative action to take is to initiate a particular software routine.

After the timer is stopped and/or other appropriate action is taken in connection with the step 914, the routine 900 may proceed to a step 916, wherein feedback is provided to the user regarding the completed event. Feedback may be provided to the user in any of a number of ways, and the invention is not limited to any particular feedback format. The user may, for example, be provided with a digital representation of a time measured by a timer started and/or stopped in connection with the steps 910 and 914. Alternatively, the time measured by such a timer may be compared with threshold values, and one or more of a group of lights may be illuminated (e.g., on the visual indicator 216 or the visual indicator 410), or one of a number of possible sounds may be emitted (e.g., by the audio indicator 214 or the audio indicator 408) to indicate, for example, a level achieved by the person on a graduated scale of speed levels. As shown in FIG. 9, after completing the step 916, the routine 900 may return to the step 902. In one embodiment, several variables or parameters may be input by the user for use by the routine 900 described above. These variables or parameters may be input, for example, via the user interface 210 of the motion-sensitive device 102 or via the user interface 404 of one of the separate devices 104. For example: (1) the threshold values for the positive and/or negative spike events may be adjusted, (2) the time periods used in connection with steps 904, 906 and 912 may be altered, (3) the particular form or type of feedback provided to the user in the step 916 may be altered, or (4) one of a number of software routines other than the routine 900 may be selected.

Such parameters or variables may have default values pre-programmed into the system, which default values may then be adjusted by the user according to certain user-specific criteria such as height, weight, or shoe hardness. Alternatively, the parameters or variables may be adjusted automatically via software, based upon this or other information input by the user.

Having thus described at least one illustrative embodiment of the invention various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A method for monitoring movement of a person in locomotion on foot, comprising steps of:
   (a) mounting a sensor on the person;
   (b) using the sensor to generate a signal in response to movement of the person;
   (c) analyzing the signal to identify a first characteristic in the signal that indicates when the person has taken an initial footstep to begin walking or running after having been stationary;
   (d) analyzing the signal to identify a second characteristic in the signal that indicates when the person has initially ceased taking footsteps after having been walking or running; and
   (e) determining an elapsed time period between when the first and second characteristics appeared in the signal.

2. The method of claim 1, wherein the step (e) includes steps of:
   (e1) in response to identifying the first characteristic, starting a timer; and
   (e2) in response to identifying the second characteristic, stopping the timer.

3. The method of claim 1, wherein the step (c) includes a step of:
   (c1) identifying the first characteristic by determining that an amplitude of the signal has exceeded a threshold.

4. The method of claim 3, wherein the step (d) includes a step of:
   (d1) identifying the second characteristic by determining that the amplitude of the signal has not exceeded a threshold for a given period of time.

5. The method of claim 1, wherein the step (d) includes a step of:
   (d1) identifying the second characteristic by determining that an amplitude of the signal has not exceeded a threshold for a given period of time.

6. The method of claim 1, wherein:
   the method further includes a step of (f) analyzing the signal to identify that the person is stationary; and
   the step (c) is performed in response to it being identified in the step (f) that the person is stationary.

7. The method of claim 6, wherein the step (f) includes a step of:
   (f1) identifying that the person is stationary by determining that an amplitude of the signal has not exceeded a threshold for a given period of time.

8. The method of claim 1, wherein the step (a) includes a step of:
   (a1) providing the sensor such that the sensor includes an accelerometer that does not require compression forces thereon to sense acceleration.

9. The method of claim 1, wherein the step (a) includes a step of:
   (a1) mounting the sensor on a foot of the person.

10. The method of claim 1, wherein the first characteristic in the signal is indicative of at least a portion of a foot of the person leaving a surface.

11. The method of claim 1, further including a step of:
    (f) beginning to attempt to identify the first characteristic in the signal in response to a user input.

12. A system for monitoring movement of a person in locomotion on foot, comprising:
    a sensor to be mounted on the person to generate a signal in response to movement of the person; and
    at least one controller coupled to the sensor to receive the signal therefrom, the at least one controller being configured to analyze the signal to identify a first characteristic in the signal that indicates when the person has taken an initial footstep to begin walking or running after having been stationary, and to analyze the signal to identify a second characteristic in the signal that indicates when the person has initially ceased taking footsteps after having been walking or running, the at least one controller being further configured to determine an elapsed time period between when the first and second characteristics appeared in the signal.

13. A method for monitoring movement of a person in locomotion on foot, comprising steps of:
    (a) mounting a sensor on the person;
    (b) using the sensor to generate a signal in response to movement of the person;
    (c) after the person has begun walking or running, analyzing the signal to identify a characteristic in the signal that indicates the person has initially ceased taking footsteps; and
    (d) determining an elapsed time period based on a time at which the characteristic appeared in the signal.

14. The method of claim 13, wherein the step (c) includes a step of:
    (c1) identifying the characteristic by determining that an amplitude of the signal has not exceeded a threshold for a given period of time.

15. The method of claim 13, wherein the step (d) includes a step of:
    (d1) stopping a timer in response to identifying the characteristic.

16. The method of claim 13, wherein the step (a) includes a step of:
    (a1) providing the sensor such that the sensor includes an accelerometer that does not require compression forces thereon to sense acceleration.

17. The method of claim 13, wherein the step (a) includes a step of:
    (a1) mounting the sensor on a foot of the person.

18. A system for monitoring movement of a person in locomotion on foot, comprising:
    a sensor to be mounted on the person to generate a signal in response to movement of the person; and
    at least one controller coupled to the sensor to receive the signal therefrom, the at least one controller being configured to analyze the signal to identify a characteristic in the signal that indicates when the person has initially ceased taking footsteps after having been walking or running, and to determine an elapsed time period based on a time at which the characteristic appeared in the signal.

19. A method for monitoring movement of a person, comprising steps of:
    (a) mounting a sensor on a foot of the person;
    (b) using the sensor to generate a signal in response to movement of the foot of the person;
    (c) analyzing the signal to identify a first characteristic in the signal indicative of the foot of the person initially beginning to move after having been stationary;
    (d) analyzing the signal to identify a second characteristic in the signal indicative of the foot of the person initially ceasing to move after having been in motion; and
    (e) determining an elapsed time period between when the first and second characteristics appeared in the signal.

20. The method of claim 19, wherein the step (e) includes steps of:
(e1) in response to identifying the first characteristic, starting a timer; and
(e2) in response to identifying the second characteristic, stopping the timer.

21. The method of claim 19, wherein the step (c) includes a step of:
(c1) identifying the first characteristic in the signal by determining that an amplitude of the signal has exceeded a threshold.

22. The method of claim 19, wherein the step (d) includes a step of:
(d1) identifying the second characteristic in the signal by determining that the amplitude of the signal has not exceeded a threshold for a given period of time.

23. The method of claim 19, wherein the step (a) includes a step of:
(a1) providing the sensor such that the sensor includes an accelerometer that does not require compression forces thereon to sense acceleration.

24. The method of claim 19, wherein the first characteristic in the signal is indicative of at least a portion of the foot leaving a surface.

25. The method of claim 19, further including a step of:
(f) beginning to attempt to identify the first characteristic in the signal in response to a user input.

26. A system for monitoring movement of a person, comprising:
a sensor to be mounted on a foot of the person to generate a signal in response to movement of the foot of the person; and
at least one controller coupled to the sensor to receive the signal therefrom, the at least one controller being configured to identify a first characteristic in the signal indicative of the foot of the person initially beginning to move after having been stationary, and to identify a second characteristic in the signal indicative of the foot initially ceasing to move after having been in motion, the at least one controller being further configured to determine an elapsed time period between when the first and second characteristics appeared in the signal.

27. A method for monitoring movement of a person, comprising steps of:
(a) mounting a sensor on a foot of the person;
(b) using the sensor to generate a signal in response to movement of the foot of the person;
(c) after a foot of the person has been in motion, analyzing the signal to identify a characteristic in the signal indicative of the foot initially ceasing to be in motion; and
(d) measuring an elapsed time period based on a time at which the characteristic appeared in the signal.

28. The method of claim 27, wherein the step (c) includes a step of:
(c1) identifying the characteristic by determining that an amplitude of the signal has not exceeded a threshold for a given period of time.

29. The method of claim 27, wherein the step (d) includes a step of:
(d1) stopping a timer in response to identifying the characteristic.

30. The method of claim 27, wherein the step (a) includes a step of:
(a1) providing the sensor such that the sensor includes an accelerometer that does not require compression forces thereon to sense acceleration.

31. A system for monitoring movement of a person, comprising:
a sensor to be mounted on a foot of the person to generate a signal in response to movement of the foot of the person; and
at least one controller coupled to the sensor to receive the signal therefrom, the at least one controller being configured to, after the foot of the person has been in motion, analyze the signal to identify a characteristic in the signal indicative of the foot initially ceasing to be in motion, and to determine an elapsed time period based on a time at which the characteristic appeared in the signal.

32. A method for monitoring movement of a person in locomotion on foot, comprising steps of:
(a) mounting a sensor on the person;
(b) using the sensor to generate a signal in response to movement of the person;
(c) analyzing the signal to identify that the person is not walking or running;
(d) in response to identifying that the person is not walking or running, analyzing the signal to identify a first characteristic in the signal that indicates the person has begun walking or running; and
(e) in response to identifying the first characteristic, taking a first action.

33. The method of claim 32, further comprising steps of:
(f) after taking the first action, analyzing the signal to identify a second characteristic in the signal that indicates the person has ceased walking or running; and
(g) in response to identifying the second characteristic, taking a second action.

34. The method of claim 32 wherein the step (d) includes a step of:
(d1) identifying the first characteristic in the signal by determining that an amplitude of the signal has exceeded a threshold.

35. The method of claim 33 wherein the step (f) includes a step of:
(f1) identifying the second characteristic in the signal by determining that an amplitude of the signal has not exceeded a threshold for a given period of time.

36. The method of claim 35 wherein the step (d) includes a step of:
(d1) identifying the first characteristic in the signal by determining that an amplitude of the signal has exceeded a threshold.

37. The method of claim 33, wherein:
the step (e) includes a step of starting a timer in response to identifying the first characteristic, and
the step (g) includes a step of stopping the timer in response to identifying the second characteristic.

38. The method of claim 32, wherein the step (a) includes a step of:
(a1) providing the sensor such that the sensor includes an accelerometer that does not require compression forces thereon to sense acceleration.

39. The method of claim 32, wherein the step (a) includes a step of:
(a1) mounting the sensor on a foot of the person.

40. The method of claim 32, wherein the first characteristic in the signal is indicative of at least a portion of a foot of the person leaving a surface.

41. The method of claim 32, wherein the step (e) includes a step of:

(e1) starting a timer in response to identifying the first characteristic.

42. The method of claim 32, wherein the step (c) includes a step of:
(c1) identifying that the person is not walking or running by determining that an amplitude of the signal has not exceeded a threshold for a given period of time.

43. A system for monitoring movement of a person in locomotion on foot, comprising:
a sensor to be mounted on the person to generate a signal in response to movement of the person; and
at least one controller coupled to the sensor to receive the signal therefrom, the at least one controller being configured to analyze the signal to identify that the person is not walking or running, to, in response to identifying that the person is not walking or running, analyze the signal to identify a first characteristic in the signal that indicates the person has begun walking or running, and to, in response to identifying the first characteristic, take a first action.

44. A method for monitoring movement of a person, comprising steps of:
(a) mounting a sensor on a foot of the person;
(b) using the sensor to generate a signal in response to movement of the foot of the person;
(c) analyzing the signal to identify that the foot of the person is stationary;
(d) in response to identifying that the foot is stationary, analyzing the signal to identify a first characteristic in the signal that indicates the foot is in motion; and
(e) in response to identifying the first characteristic, taking a first action.

45. The method of claim 44, further including steps of:
(f) after taking the first action, analyzing the signal to identify a second characteristic in the signal that indicates the foot has become stationary; and
(g) in response to identifying the second characteristic, taking a second action.

46. The method of claim 44, wherein the step (d) includes a step of:
(d1) determining that an amplitude of the signal has exceeded a threshold.

47. The method of claim 45, wherein the step (f) includes a step of:
(f1) determining that the amplitude of the signal has not exceeded a threshold for a given period of time.

48. The method of claim 47, wherein the step (d) includes a step of:
(d1) determining that an amplitude of the signal has exceeded a threshold.

49. The method of claim 45, wherein:
the step (e) includes a step of starting a timer in response to identifying the first characteristic; and
the step (g) includes a step of stopping the timer in response to identifying the second characteristic.

50. The method of claim 44, wherein the step (a) includes a step of:
(a1) providing the sensor such that the sensor includes an accelerometer that does not require compression forces thereon to sense acceleration.

51. The method of claim 44, wherein the first characteristic in the signal is indicative of at least a portion of the foot leaving a surface.

52. The method of claim 44, wherein the step (d) includes a step of:
(d1) identifying that the foot of the person is in motion by determining that an amplitude of the signal has exceeded a threshold.

53. The method of claim 44, wherein the step (e) includes a step of starting a timer in response to identifying the first characteristic.

54. The method of claim 44, wherein the step (c) includes a step of:
(c1) identifying that the foot of the person is stationary by determining that an amplitude of the signal has not exceeded a threshold for a given period of time.

55. A system for monitoring movement of a person, comprising:
a sensor to be mounted on a foot of the person to generate a signal in response to movement of the foot of the person; and
at least one controller coupled to the sensor to receive the signal therefrom, the at least one controller being configured analyze the signal to identify that the foot of the person is stationary, to, in response to identifying that the foot is stationary, analyze the signal to identify a first characteristic in the signal that indicates the foot is in motion, and to, in response to identifying the first characteristic, take a first action.

56. The method of claim 1, wherein the second characteristic represents a first time the person did not take a footstep when a footstep would have been expected to have been taken by the person if the person had continued walking or running.

57. The method of claim 1, wherein the step (a) includes a step of (a1) mounting the sensor below a waist of the person.

58. The method of claim 57, wherein the step (a1) includes a step of:
providing the sensor such that the sensor includes an accelerometer that does not require compression forces thereon to sense acceleration.

59. The method of claim 1, wherein the step (d) is performed after the step (c).

60. The method of claim 9, wherein the step (a1) includes a step of:
providing the sensor such that the sensor includes including an accelerometer that does not require compression forces thereon to sense acceleration.

61. The system of claim 13, wherein the at least one controller is further configured to start a timer in response to identifying the first characteristic, and to stop the timer in response to identifying the second characteristic.

62. The system of claim 12, wherein the second characteristic represents a first time the person did not take a footstep when a footstep would have been expected to have been taken by the person if the person had continued walking or running.

63. The system of claim 12, wherein the sensor includes an accelerometer that does not require compression forces thereon to sense acceleration.

64. The system of claim 12, wherein the first characteristic in the signal is indicative of at least a portion of a foot of the person leaving a surface.

65. The system of claim 12, wherein the at least one controller is further configured to begin to attempt to identify the first characteristic in the signal in response to a user input.

66. The method of claim 13, wherein the step (d) includes a step of (d1) measuring the elapsed time period so that the elapsed time period ends at the time at which the characteristic appeared in the signal.

67. The method of claim 13, wherein the characteristic in the signal represents a first time the person did not take a footstep when a footstep would have been expected to have been taken by the person if the person had continued walking or running.

68. The method of claim 13, wherein the step (a) includes a step of (a1) mounting the sensor below a waist of the person.

69. The method of claim 68, wherein the step (a1) includes a step of:

providing the sensor such that the sensor includes an accelerometer that does not require compression forces thereon to sense acceleration.

70. The system of claim 18, wherein the at least one controller is further configured to stop a timer in response to identifying the characteristic.

71. The system of claim 18, wherein the sensor includes an accelerometer that does not require compression forces thereon to sense acceleration.

72. The method of claim 19, wherein the step (d) is performed after the step (c).

73. The system of claim 26, wherein the at least one controller is further configured to start a timer in response to identifying the first characteristic, and to stop the timer in response to identifying the second characteristic.

74. The system of claim 26, wherein the sensor includes an accelerometer that does not require compression forces thereon to sense acceleration.

75. The system of claim 26, wherein the first characteristic in the signal is indicative of at least a portion of the foot leaving a surface.

76. The system of claim 26, wherein the at least one controller is further configured to begin to attempt to identify the first characteristic in the signal in response to a user input.

77. The system of claim 31, wherein the at least one controller is further configured to stop a timer in response to identifying the characteristic.

78. The system of claim 31, wherein the sensor includes an accelerometer that does not require compression forces thereon to sense acceleration.

79. The method of claim 39, wherein the step (a1) includes a step of:

providing the sensor such that the sensor includes including an accelerometer that does not require compression forces thereon to sense acceleration.

80. The method of claim 32, wherein the step (a) includes a step of:

(a1) mounting the sensor below a waist of the person.

81. The method of claim 80, wherein the step (a1) includes a step of:

providing the sensor such that the sensor includes including an accelerometer that does not require compression forces thereon to sense acceleration.

82. The system of claim 43, wherein the at least one controller is further configured to, after taking the first action, analyze the signal to identify a second characteristic in the signal that indicates the person has ceased walking or running, and to, in response to identifying the second characteristic, take a second action.

83. The system of claim 82, wherein the at least one controller is further configured to start a timer in response to identifying the first characteristic, and to stop the timer in response to identifying the second characteristic.

84. The system of claim 43, wherein the sensor includes an accelerometer that does not require compression forces thereon to sense acceleration.

85. The system of claim 43, wherein the first characteristic in the signal is indicative of at least a portion of a foot of the person leaving a surface.

86. The system of claim 43, wherein the at least one controller is further configured to start a timer in response to identifying the first characteristic.

87. The system of claim 55, wherein the at least one controller is further configured to, after taking the first action, analyze the signal to identify a second characteristic in the signal that indicates the foot has become stationary, and to, in response to identifying the second characteristic, take a second action.

88. The system of claim 87, wherein the at least one controller is further configured to start a timer in response to identifying the first characteristic, and to stop the timer in response to identifying the second characteristic.

89. The system of claim 55, wherein the sensor includes an accelerometer that does not require compression forces thereon to sense acceleration.

90. The system of claim 55, wherein the first characteristic in the signal is indicative of at least a portion of the foot leaving a surface.

91. The system of claim 55, wherein the at least one controller is further configured to start a timer in response to identifying the first characteristic.

\* \* \* \* \*